US012642913B2

(12) United States Patent
Denyer et al.

(10) Patent No.: US 12,642,913 B2
(45) Date of Patent: Jun. 2, 2026

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,222

(22) Filed: Aug. 29, 2024

(65) Prior Publication Data

US 2026/0061137 A1     Mar. 5, 2026

(51) Int. Cl.
A61M 5/32     (2006.01)

(52) U.S. Cl.
CPC ................................. A61M 5/3204 (2013.01)

(58) Field of Classification Search
CPC .... A61M 5/3204; A61M 5/32; A61M 5/3202; A61M 5/321; A61M 5/3271; A61M 5/3272; A61M 5/326; A61M 5/3257; A61M 2005/3268; A61M 2005/3261; A61M 2005/3267; A61M 5/31; A61M 5/31568; A61M 5/322; A61M 5/3269
See application file for complete search history.

(56) References Cited

U.S. PATENT DOCUMENTS

| 4,118,611 A | 10/1978 | Harris |
| 4,994,045 A | 2/1991 | Ranford |
| | (Continued) | |

FOREIGN PATENT DOCUMENTS

| EP | 1024845 B1 | 7/2003 |
| EP | 3204066 B1 | 5/2019 |
| | (Continued) | |

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.
(Continued)

*Primary Examiner* — Chelsea E Stinson
*Assistant Examiner* — Hamza A Darb
(74) *Attorney, Agent, or Firm* — Fish & Richardson P.C.

(57) ABSTRACT
A medicament delivery device has a needle for injecting medicament into a user, a body having a proximal end and a distal end and a needle cover. The needle cover is axially movable relative to the body between an initial position, in which the needle cover covers the distal end of the needle, and a holding position. In the holding position the needle protrudes from the distal end of the needle cover. The needle cover has a flexible arm. The device further has a needle cover guide comprising a track. The flexible arm engages the track. The track has a radially-extending ramp configured to flex the flexible arm when the needle cover moves from the initial position to the holding position. The flexible arm is flexed when the needle cover is in the holding position.

17 Claims, 4 Drawing Sheets

(56)                    References Cited

U.S. PATENT DOCUMENTS

| | | | |
|---|---|---|---|
| 6,547,764 B2* | 4/2003 | Larsen ................ | A61M 5/3272 |
| | | | 604/110 |
| 8,858,510 B2 | 10/2014 | Karlsson | |
| 9,919,107 B2 | 3/2018 | Imai et al. | |
| 10,881,797 B2 | 1/2021 | Bostrom | |
| 12,011,570 B2 | 6/2024 | Kemp et al. | |
| 12,329,952 B1 | 6/2025 | Denyer et al. | |
| 2002/0133122 A1 | 9/2002 | Giambattista et al. | |
| 2007/0078408 A1 | 4/2007 | Wang | |
| 2012/0041368 A1* | 2/2012 | Karlsson ............. | A61M 5/3272 |
| | | | 604/111 |
| 2013/0131590 A1 | 5/2013 | Olson et al. | |
| 2019/0282761 A1 | 9/2019 | Wilson et al. | |
| 2020/0282151 A1 | 9/2020 | Liscio | |
| 2022/0143325 A1 | 5/2022 | Yeh | |
| 2024/0033443 A1 | 2/2024 | Dasbach et al. | |
| 2024/0261517 A1 | 8/2024 | Forster et al. | |

FOREIGN PATENT DOCUMENTS

| | | |
|---|---|---|
| WO | WO 2006/111860 A1 | 10/2006 |
| WO | WO 2020/014292 A1 | 1/2020 |
| WO | WO 2022/117682 A1 | 6/2022 |
| WO | WO 2023/104512 A1 | 6/2023 |
| WO | WO 2025/207897 A1 | 10/2025 |

OTHER PUBLICATIONS

Speciale et al., "Snap-Through Buckling Mechanism for Frequency-up Conversion in Piezoelectric Energy Harvesting," Applied Sciences, May 23, 2020, 10(10):3614, 18 pages.

U.S. Appl. No. 18/819,371, filed Aug. 29, 2024, Timothy Denyer.

U.S. Appl. No. 18/819,040, filed Aug. 29, 2024, Timothy Denyer.

International Search Report and Written Opinion in International Appln. No. PCT/US2025/030561, mailed on Aug. 6, 2025, 19 pages.

International Search Report and Written Opinion in International Appln. No. PCT/US2025/041621, mailed on Nov. 24, 2025, 18 pages.

International Search Report and Written Opinion in International Appln. No. PCT/US2025/043757, mailed on Dec. 4, 2025, 20 pages.

* cited by examiner

MEDICAMENT DELIVERY DEVICE

TECHNICAL FIELD

This application relates to a medicament delivery device and a method of using a medicament delivery device.

BACKGROUND

Medicament delivery devices are used to deliver a range of medicaments.

In some devices, the device must be held in a holding position at an injection site, to ensure that the correct dose of medicament is dispensed from the device, before removing the device from the injection site.

It may be difficult to hold the device in the holding position whilst the medicament is dispensed. This may result in pain, discomfort, a wet injection site, early device removal and/or partial delivery of the medicament.

It is an aspect of the present disclosure to provide an improved medicament delivery device.

SUMMARY

According to a first aspect of the present disclosure, there is provided a medicament delivery device comprising a needle for injecting medicament; a body having a proximal end and a distal end; a needle cover, wherein the needle cover is proximally movable relative to the body between an initial position, in which the needle cover covers the distal end of the needle, and a holding position for dispensing medicament from the device, wherein in the holding position the needle protrudes from the distal end of the needle cover, wherein the needle cover comprises a flexible arm; a biasing member configured to bias the needle cover distally; and a needle cover guide comprising a track, wherein the flexible arm engages the track, and wherein the track comprises a radially-extending ramp configured to flex the flexible arm when the needle cover moves from the initial position to the holding position, and wherein the flexible arm is flexed when the needle cover is in the holding position.

The needle cover guide may be rotatable relative to the body, and wherein the track extends at least partially around the circumference of the needle cover guide for rotating the needle cover guide when the needle cover moves from the initial position to the holding position.

The flexible arm may comprise a protrusion, and wherein the flexible arm engages the track via the protrusion.

The track may comprise a first region and a second region. The protrusion may travel from the first region to the second region when the needle cover moves from the initial position to the holding position.

The first region may comprise the radially-extending ramp. The first region may comprise a barrier for engaging the protrusion to prevent or restrict rotation of the needle cover guide when the protrusion travels along the radially-extending ramp.

The second region may extend at least partially around the circumference of the needle cover guide.

The second region may be at an acute angle relative to the axis of the device.

The needle cover may be distally movable relative to the body between the holding position and a locked position, wherein the needle cover covers the distal end of the needle in the locked position.

The medicament delivery device may comprise a locking surface, and wherein the needle cover engages the locking surface when the needle cover is in the locked position for preventing proximal movement of the needle cover.

The flexible arm may engage the locking surface when the needle cover is in the locked position for preventing proximal movement of the needle cover. The protrusion may engage the locking surface when the needle cover is in the locked position for preventing proximal movement of the needle cover.

The locking surface may be provided on the needle cover guide.

The track may comprise an axially-extending region, and wherein the flexible arm engages the axially-extending region when the needle cover moves from the holding position to the locked position.

The medicament delivery device may be configured to inject greater than 2 ml of medicament and/or the medicament delivery device may be configured to inject medicament having a viscosity of greater than 25 cP.

The medicament delivery device may comprise the medicament.

According to another aspect of the present disclosure, there is provided method of using a medicament delivery device prior to dispensing medicament from the device, the method comprising moving a needle cover of the device proximally relative to a body of the device towards a holding position, wherein the needle cover comprises a flexible arm which engages a track comprising a radially-extending ramp, and wherein when the needle cover is moved towards the holding position then the flexible arm is flexed by the radially-extending ramp.

According to another aspect of the present disclosure, there is provided method of using a medicament delivery device, the method comprising pressing a needle cover of the device against an injection site to move the needle cover towards a holding position, wherein the needle cover comprises a flexible arm which engages a track comprising a radially-extending ramp, and wherein the flexible arm is flexed by the radially-extending ramp when the needle cover is moved towards the holding position; applying a holding force to the device to hold the needle cover against the injection site whilst medicament is dispensed from the device, wherein the flexible arm is flexed when the holding force is applied to the device; and removing the device from the injection site.

The method may first comprise removing a cap from the medicament delivery device.

The rotation of the collar may cause medicament to be dispensed from the device via the needle.

The movement of the needle cover from the initial position to the holding position may cause medicament to be dispensed from the device via the needle.

The device may comprise a mechanism configured to dispense medicament from the device via the needle when the needle cover reaches a predetermined axial position. Movement of the needle cover from the initial position to the holding position may trigger the mechanism to dispense medicament from the device via the needle.

The medicament delivery device may comprise a container for containing the medicament. The medicament may be located in the container. The container may be a syringe. The syringe may comprise the needle. The container may be a cartridge which is initially separated from the needle when the needle cover is in the initial position.

BRIEF DESCRIPTION OF THE FIGURES

Embodiments will now be described, by way of example only, with reference to the accompanying drawings, in which.

DETAILED DESCRIPTION

Figures 1A, 1B:
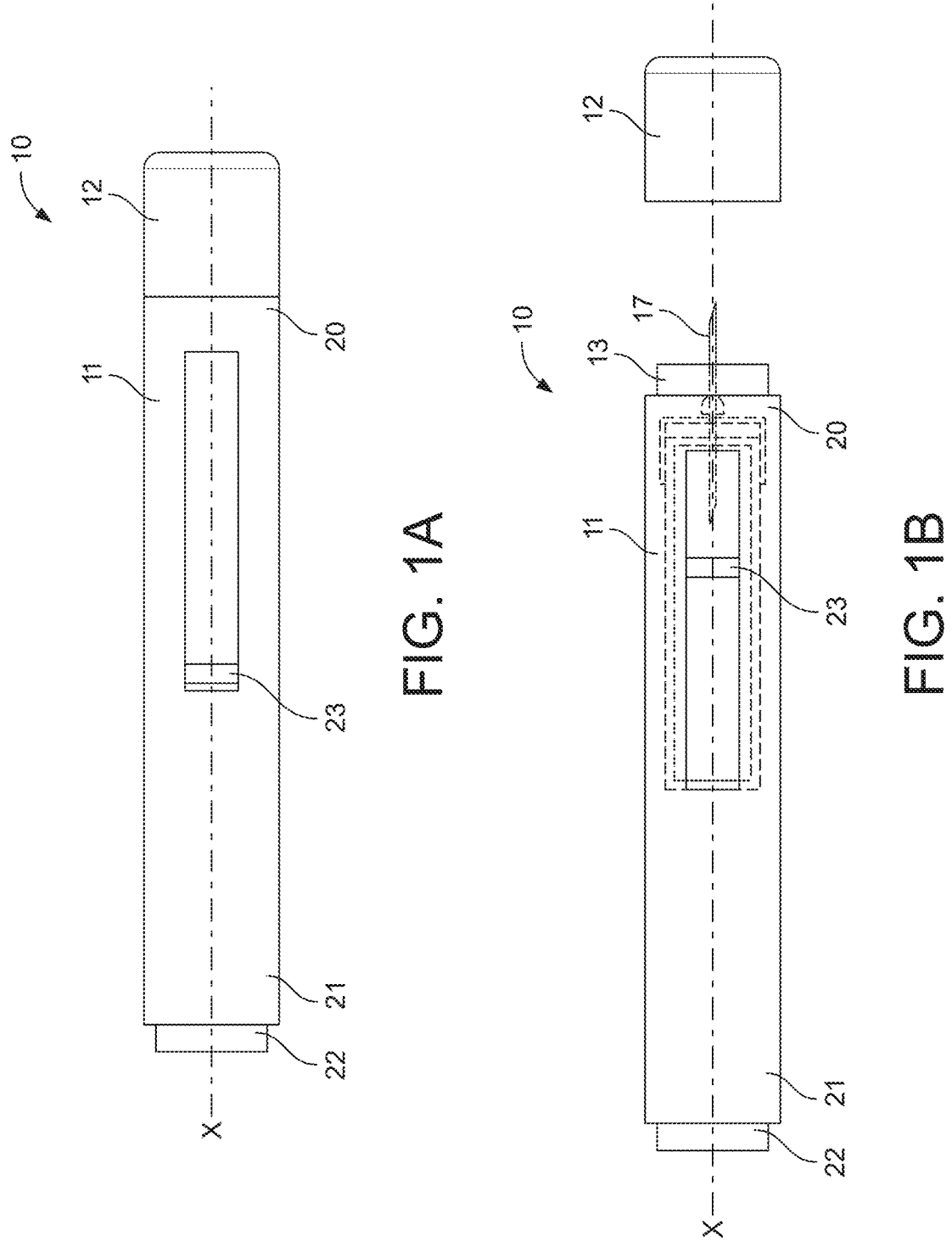
FIG. 1A shows an injector device with a cap attached.
FIG. 1B shows the injector device of FIG. 1A with the cap removed.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
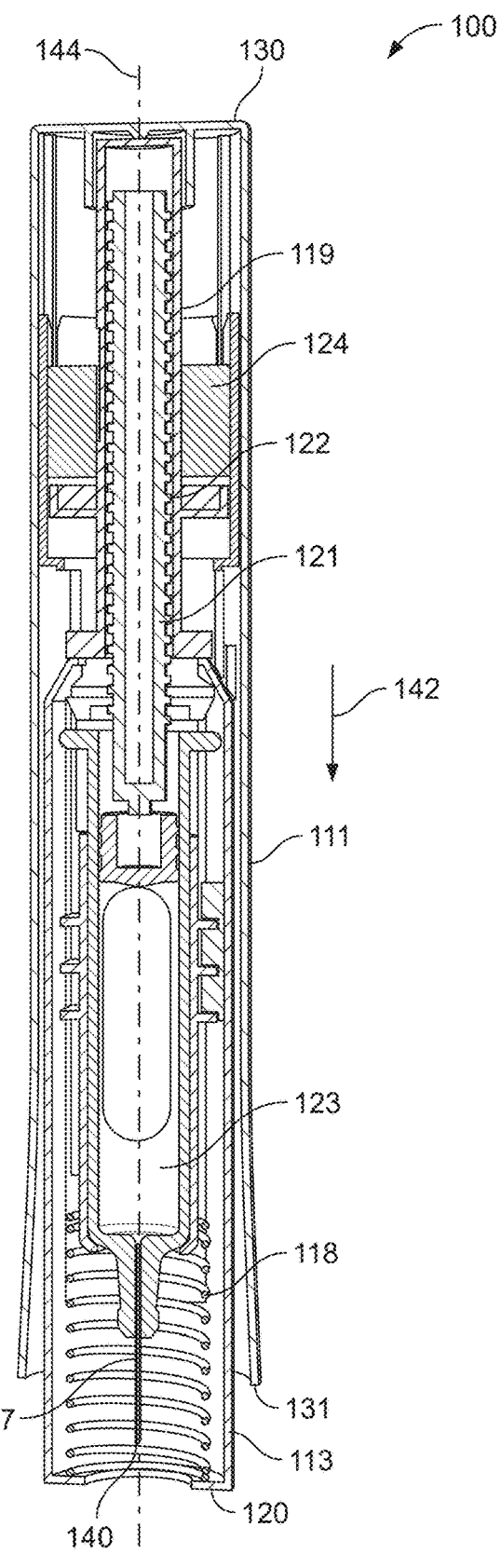
FIG. 2 shows an injector device.

FIG. 2 shows a simplified view of a medicament delivery device 100. The medicament delivery device 100 has a needle 117 for injecting medicament into a user, a body 111 having a proximal end 130 and a distal end 131, and a needle cover 113. The needle 117 has a distal end 140. The needle cover 113 is proximally movable relative to the body 111 between an initial position, in which the needle cover 113 covers the distal end 140 of the needle, and a holding position for dispensing medicament from the device. The device 100 extends along an axis 144.

The device 100 is shown in the initial position in FIG. 2. In the holding position the needle cover 113 is located proximally relative to the initial position. In the holding position the needle 117 protrudes from the distal end 120 of the needle cover 113.

The medicament delivery device further comprises a biasing member such as a spring 118 configured to bias the needle cover 113 axially in the distal direction. The distal direction is indicated by the direction of the arrow 142 in FIG. 2.

The medicament delivery device has a plunger 121 which is axially movable within a syringe 123 of the device to dispense medicament from the syringe 123 via the needle 117.

The medicament delivery device has a collar 119. The collar 119 is axially fixed relative to the body 111. The collar 119 interfaces with the plunger 121 via a screw thread 122. The medicament delivery device 100 has a biasing member such as a spring 124 that is configured to rotate the collar 119 when the spring 124 is released. The spring 124 may be a torsion spring. The spring 124 is released when the needle cover 113 reaches a predetermined axial displacement with a release mechanism (not shown). The rotation of the collar 119 causes the plunger 121 to move distally within the syringe 123, in view of the screw thread 122, to thereby dispense medicament from the syringe 123 via the needle 117.

The needle cover 113 is pressed against an injection site, thereby moving the needle cover 113 axially into the body 111 and uncovering the needle 117. The axial displacement of the needle cover 113 causes the release of the spring 124 which rotates the collar 119. The rotation of the collar 119 moves the plunger 121 axially within the syringe 123 to dispense the medicament via the needle 117.

The device 100 is pressed against the injection site 125, to hold the needle cover 113 at the holding position whilst the medicament is dispensed from the device.

After the medicament has been dispensed, the device 100 is removed from the injection site. The needle cover 113 moves distally under the force of the spring 118 to a locked position. In the locked position, the needle cover 113 covers the distal end 140 of the needle. In the locked position, the needle cover is prevented from moving proximally.

The medicament delivery device 100 is configured to inject greater than 2 ml of medicament and/or the medicament delivery device 100 is configured to inject medicament having a viscosity of greater than 25 cP.

Figures 3A, 3B, 3C:
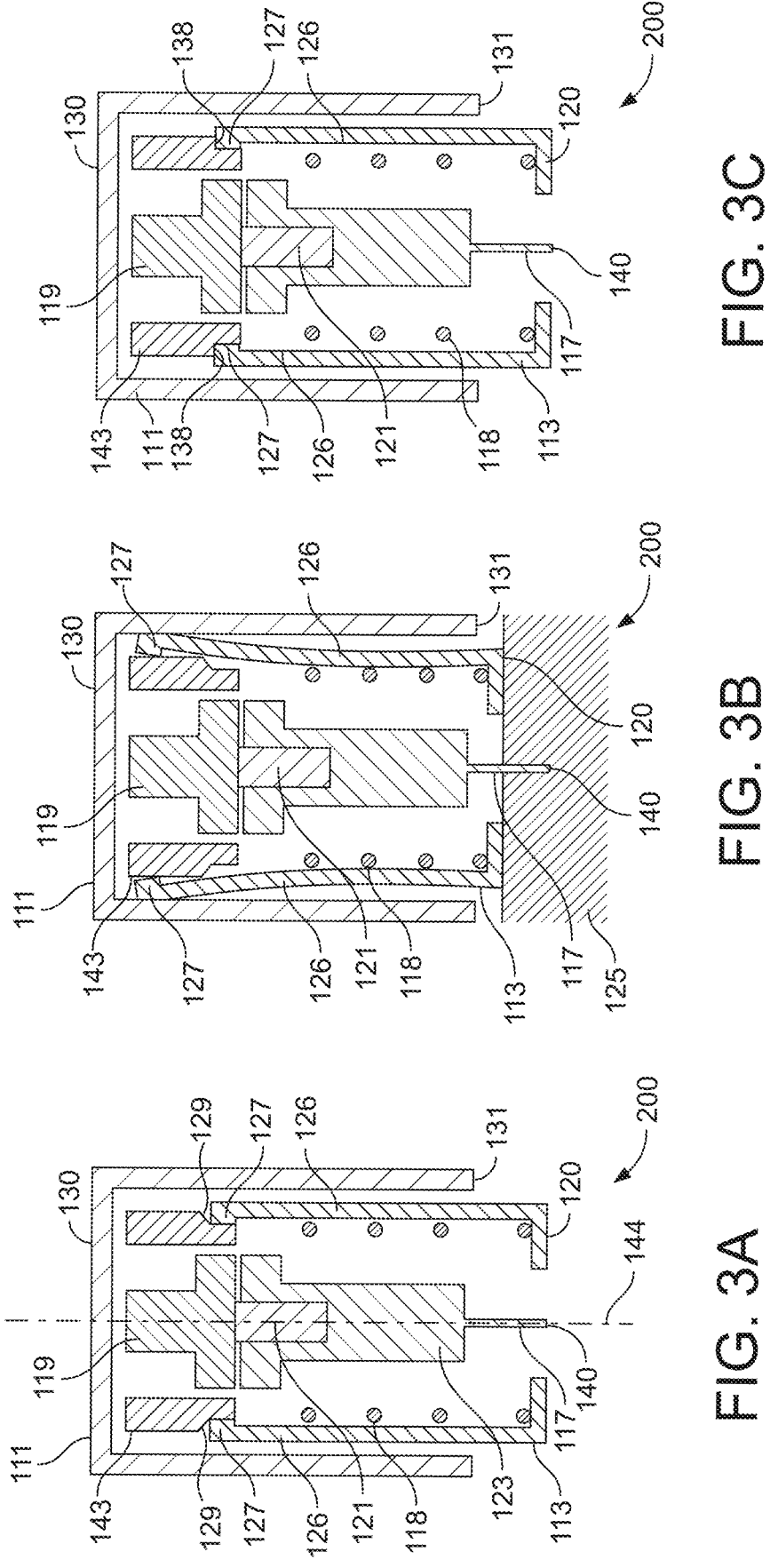
FIG. 3A shows a simplified view of an example injector device when the needle cover is in the initial position.
FIG. 3B shows a simplified view of the device of FIG. 3A when the needle cover is in the holding position.
FIG. 3C shows a simplified view of the device of FIG. 3A when the needle cover is in the locked position.

FIGS. 3A to 3C show a simplified view of a medicament delivery device 200. The features described and/or contemplated in relation to the medicament delivery device 200 may be incorporated in the medicament delivery device 100 described and/or contemplated above.

The features described and/or contemplated in relation to the medicament delivery device 200 may be incorporated in another medicament delivery device, for example a medicament delivery device having a different mechanism for dispensing medicament to that described in relation to the medicament delivery device 100, and/or a medicament delivery device which is configured to inject 2 ml or less of medicament and/or a medicament delivery device which is configured to inject medicament having a viscosity of 25 cP or less, and/or a medicament delivery device in which the medicament is contained in a cartridge which is initially separated from the needle when the needle cover is in the initial position.

In FIGS. 3A to 3C, the reference numerals correspond to corresponding features described and/or contemplated above in relation to FIG. 2.

In FIG. 3A, the medicament delivery device 200 is shown in the initial position. In FIG. 3B the device 200 is shown in the holding position. In FIG. 3C the device 200 is shown in the locked position.

The needle cover 113 of the medicament delivery device 200 has a pair of flexible arms 126. Although in another embodiment, the needle cover 113 may have a single flexible arm 126 or more than two flexible arms 126.

The or each flexible arm 126 has a protrusion 127. The protrusion is at the free end of the or each flexible arm although in another embodiment the protrusion may be located distally from the free end of the flexible arm.

Figure 4:
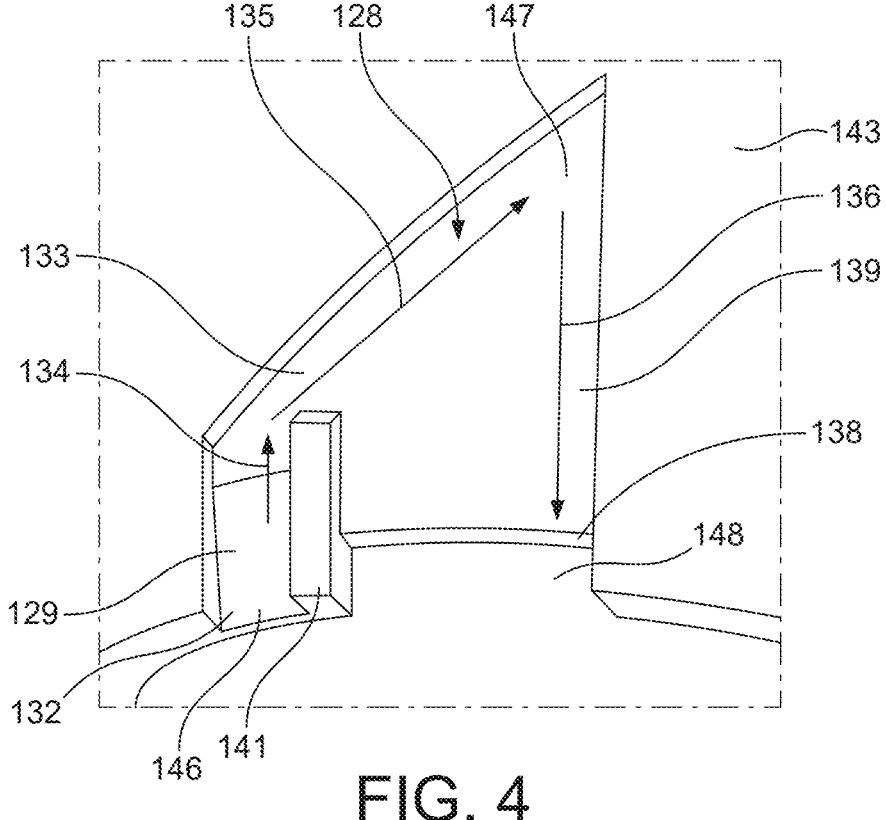
FIG. 4 shows a view of the track of the injection device of FIG. 3A.

The medicament delivery device 200 has a needle cover guide 143 comprising a track 128. The track 128 is shown in FIG. 4. The needle cover guide 143 may provide a separate track 128 for each flexible arm.

The flexible arm 126 engages the track 128 via the protrusion 127. When the needle cover 113 is in the initial position the flexible arm 126 engages the track 128 via the protrusion 127 at the first position (see FIG. 4). The track 128 comprises a radially-extending ramp 129 configured to flex the flexible arm 126 when the needle cover 113 move from the initial position to the holding position.

The flexible arm 126 is positioned radially outwardly of the needle cover guide 143. The radially-extending ramp 129 is configured to flex the flexible arm 126 radially outwards. In another embodiment, the flexible arm is positioned radially inwardly of the needle cover guide, and the radially-extending ramp 129 is configured to flex the flexible arm 126 radially inwards.

The flexible arm is flexed by the radially-extending ramp 129 when the protrusion 127 travels proximally along the radially-extending ramp. The flexible arm 126 remains flexed when the needle cover is in the holding position. When the needle cover 113 is in the holding position the flexible arm 126 engages the track 128 via the protrusion 127 at the second position 147 (see FIG. 4). The friction force between the flexible arm 126, in its flexed state, and the needle cover guide 143 in the holding position, acts against the force of the biasing member such as the spring 118 to reduce the force that is applied to hold the needle cover 113 in the holding position.

The needle cover guide 143 is rotatable relative to the body 111. The track 128 extends at least partially around the circumference of the needle cover guide 143. The needle cover guide 143 rotates when the needle cover 113 moves from the initial position to the holding position.

The track comprises a first region 132 and a second region 133. The protrusion travels from the first region 132 to the second region 133 when the needle cover 113 moves from the initial position to the holding position.

When the needle cover moves from the initial position to the holding position it releases a mechanism, such as the mechanism described and/or contemplated in relation to FIG. 2, which automatically causes medicament to be dispensed from the device 200. The needle cover 113 is held in the holding position, for example for a predetermined period of time, whilst the medicament is dispensed from the device.

The first region 132 comprises the radially-extending ramp 129. The first region 132 has a barrier 141 for engaging the protrusion 127 to prevent or restrict rotation of the needle cover guide 143 when the protrusion 127 travels along the radially-extending ramp 129. In another embodiment (not shown), the second region 133 comprises the radially-extending ramp 129.

The second region 133 extends at least partially around the circumference of the needle cover guide 143. The second region 133 has an axially-extending component of direction. The second region 133 is at an acute angle relative to the axis 144 of the medicament delivery device 200. The needle cover guide 143 therefore rotates when the protrusion 127 travels along the second region 133 of the track. In an embodiment, the second region 133 may have a radially-extending ramp in addition or alternatively to the presence of the radially-extending ramp 129 in the first region 132.

When the needle cover 113 is in the holding position then the protrusion 127 is located at the section position 147 on the track 128. The second position 147 is at the end of the second region 113. The second position 147 is at the proximal end of the track 128.

After the medicament has been dispensed from the device, the device 200 is removed from the injection site 125 and the needle cover 113 moves from the holding position towards the locked position as shown, for example, in FIG. 3C. As noted, in the locked position the needle cover 113 covers the distal end 140 of the needle 117. When the needle cover 113 is in the locked position the protrusion 127 is at the third position 148.

The medicament delivery device 200 has a locking surface 138 provided on the needle cover guide 143. The locking surface 138 is in the form of an undercut or a radially-extending surface which may be orthogonal to the axis 144. The locking surface 138 extends radially to allow the flexible arm 126 to flex back towards its unflexed position when the needle cover moves from the holding position to the locked position. The protrusion 127 engages the locking surface 138 when the needle cover 113 is in the locked position for preventing proximal movement of the needle cover 113. The needle 117 therefore cannot be exposed for stick injuries after the device 200 has been used.

In another embodiment, the locking surface 138 may be provided on another component of the device 200.

In the example discussed above, it is the protrusion 127 which engages the locking surface 138 in the locked position but in another embodiment another part of the needle cover 113 may engage the locking surface 138. For example the needle cover 113 may be provided with an additional protrusion or a proximal-facing surface which engages the locking surface 138 in the locked position.

If the device did not have a locking functionality for preventing proximal movement of the needle cover after use, then the spring 118 would need to be much stronger to ensure that the distal end 140 of the needle remains covered once the device has been used. Therefore, having the locking functionality in the device means that the spring 118 can be weaker, which consequently reduces the force that is required to hold the device in the holding position.

The track 128 has an axially-extending region 139 which can also be seen as a third region of the track 128. The protrusion 127 engages the axially-extending region 139 of the track when the needle cover 113 moves from the holding position to the locked position.

The device 200 comprises a mechanism configured to dispense medicament from the device 200 via the needle 117 when the needle cover 113 reaches a predetermined axial position within the device. This mechanism may comprise a torsion spring 124, the collar 119 and the piston 121, as described above in relation to the device 100, or it may be another mechanism.

In another embodiment, the or each flexible arm 126 does not have a protrusion 127 which engages the track 128. Instead, for example, a surface of the flexible arm 126 could engage the track 128.

In another embodiment, the track 129 has a different configuration. For example, the first region of the track may also have a circumferentially-extending component of direction and/or the barrier 141 may not be present or have a different form. Additionally or alternatively the radially-extending ramp 129 may be provided on the second region 133 of the track.

In another embodiment, the first and the second regions may be indistinguishable. For example the track 128 may comprise a single region comprising the radially-extending ramp. The flexible arm would engage the single region as the needle cover 113 moves from the initial position to the holding position. The single region may extend in a direction which is parallel to the axis 144 of the device or in a direction which is at an acute angle to the axis 144 of the device.

The medicament delivery device may additionally have a cap which covers the distal end of the needle cover.

A method of using the medicament delivery device will now be described.

The method involves removing the cap (if present) from the medicament delivery device. The method then involves pressing a needle cover of the device against an injection site, applying a holding force to the device to hold the needle cover against the injection site whilst medicament is dispensed from the device, and removing the device from the injection site.

LIST OF FEATURES

10—Device
11—housing
12—cap
13—needle sleeve
17—needle
20—distal region
21—proximal region
22—button
23—piston
100—Device
111—body
113—needle cover
117—needle
118—biasing member
119—collar
120—distal end of needle cover
121—plunger
122—screw thread
123—syringe
124—torsion spring
125—injection site
126—flexible arm
127—protrusion
128—track
129—radially-extending ramp
130—proximal end of body
131—distal end of body
132—first region of track
133—second region of track
134—first arrow
135—second arrow
136—third arrow
138—locking surface
139—axially-extending region of track
140—distal end of needle
141—barrier
142—distal direction
143—needle cover guide
144—axis
146—first position
147—second position
148—third position
200—device The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®): B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A medicament delivery device comprising:
a needle for injecting medicament;
a body having a proximal end and a distal end;
a needle cover, wherein the needle cover is proximally movable relative to the body A between an initial position, in which the needle cover covers a distal end of the needle, and a holding position for dispensing medicament from the device, wherein in the holding position the A needle protrudes from a distal end of the needle cover, wherein the needle cover comprises a flexible arm;
a biasing member configured to bias the needle cover distally; and
a needle cover guide rotatable relative to the body, the needle cover guide comprising a track comprising a first region and a second region, wherein the second region extends at least a first distance partially around a circumference of the needle cover guide for rotating the needle cover guide when the needle cover moves from the initial position to the holding position,
wherein the flexible arm engages the track, and wherein the track comprises a radially-extending ramp configured to flex the flexible arm when the needle cover moves from the initial position to the holding position, and wherein the flexible arm is flexed when the needle cover is in the holding position;
wherein the needle cover is distally movable relative to the body to a locked position, wherein the needle cover covers the distal end of the needle in the locked position, wherein the medicament delivery device comprises a locking surface, and wherein the needle cover engages the locking surface when the needle cover is in the locked position for preventing proximal movement of the needle cover, wherein the locking surface comprises a radially-extending surface extending at least a second distance partially around the circumference of the needle cover guide, wherein the second distance is greater than half of the first distance.

2. The medicament delivery device of claim 1, wherein the flexible arm comprises a protrusion, and wherein the flexible arm engages the track via the protrusion.

3. The medicament delivery device of claim 2, wherein the protrusion travels from the first region to the second region when the needle cover moves from the initial position to the holding position.

4. The medicament delivery device of claim 3, wherein the first region comprises the radially-extending ramp.

5. The medicament delivery device of claim 3, wherein the second region is at an acute angle relative to the axis of the device.

6. The medicament delivery device of claim 1, wherein the locking surface is provided on the needle cover guide.

7. The medicament delivery device of claim 1, wherein the track comprises an axially-extending region, and wherein the flexible arm engages the axially-extending region when the needle cover moves from the holding position to the locked position.

8. The medicament delivery device of claim 1, wherein the medicament delivery device is configured to inject greater than 2 ml of medicament.

9. The medicament delivery device of claim 1, wherein the medicament delivery device is configured to inject medicament having a viscosity of greater than 25 cP.

10. The medicament delivery device of claim 1, wherein the radially-extending ramp is configured to flex the flexible arm radially outwards.

11. The medicament delivery device of claim 1, wherein the medicament delivery device comprises the medicament.

12. The medicament delivery device of claim 1, wherein the first region extends at least partially around the circumference of the needle cover guide.

13. The medicament delivery device of claim 1, wherein the second region comprises a radially-extending ramp.

14. A method of using a medicament delivery device prior to dispensing medicament from the device, the method comprising moving a needle cover of the device proximally relative to a body of the device towards a holding position, wherein the needle cover comprises a flexible arm which engages a track of the body, the track comprising a first region and a second region, wherein the first region comprises a radially-extending ramp, wherein the second region extends at least a first distance partially around a circumference of the body for rotating the body when the needle cover moves from an initial position to the holding position, and wherein when the needle cover is moved towards the holding position then the flexible arm is flexed by the radially-extending ramp, wherein the needle cover moves to a locked position when the device is removed from the injection site, wherein the medicament delivery device comprises a locking surface, wherein the needle cover engages the locking surface when the needle cover is in the locked position for preventing proximal movement of the needle cover, wherein the locking surface comprises a radially-extending surface extending at least a second distance partially around the circumference of the needle cover guide, wherein the second distance is greater than half of the first distance.

15. A method of using a medicament delivery device, the method comprising:

pressing a needle cover of the device against an injection site to move the needle cover towards a holding position, wherein the needle cover comprises a flexible arm which engages a rotatable body of the medicament delivery device, wherein the rotatable body comprises a track, the track comprising a first region and a second region, wherein the first region comprises a radially-extending ramp, wherein the second region extends at least a first distance partially around a circumference of the rotatable body for rotating the rotatable body when the needle cover moves from an initial position to the holding position, and wherein the flexible arm is flexed by the radially-extending ramp when the needle cover is moved towards the holding position; and applying a holding force to the device to hold the needle cover against the injection site whilst medicament is dispensed from the device, wherein the flexible arm is flexed when the holding force is applied to the device; and removing the device from the injection site, wherein the needle cover moves to a locked position when the device is removed from the injection site, wherein the medicament delivery device comprises a locking surface, wherein the needle cover engages the locking surface when the needle cover is in the locked position for preventing proximal movement of the needle cover, wherein the locking surface comprises a radially-extending surface extending at least a second distance partially around the circumference of the needle cover guide, wherein the second distance is greater than half of the first distance.

16. The method of claim 15, wherein the method first comprises removing a cap from the medicament delivery device.

17. The method of claim 15, wherein the first region comprises a barrier for engaging the protrusion to prevent or restrict rotation of the needle cover guide when the protrusion travels along the radially-extending ramp.

* * * * *